(12) United States Patent
Ishii

(10) Patent No.: US 9,581,583 B2
(45) Date of Patent: Feb. 28, 2017

(54) BLOOD ANALYSIS APPARATUS

(71) Applicant: HORIBA, Ltd., Kyoto-shi, Kyoto (JP)

(72) Inventor: Yuki Ishii, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 221 days.

(21) Appl. No.: 14/279,163

(22) Filed: May 15, 2014

(65) Prior Publication Data

US 2014/0341780 A1 Nov. 20, 2014

(30) Foreign Application Priority Data

May 17, 2013 (JP) .................................. 2013-105519

(51) Int. Cl.
| G01N 21/00 | (2006.01) |
| G01N 33/00 | (2006.01) |
| G01N 15/06 | (2006.01) |
| G01N 33/48 | (2006.01) |
| G01N 33/49 | (2006.01) |
| G01N 35/10 | (2006.01) |
| G01N 15/10 | (2006.01) |

(52) U.S. Cl.
CPC .............. *G01N 33/49* (2013.01); *G01N 15/10* (2013.01); *G01N 35/1016* (2013.01); *G01N 2015/1006* (2013.01)

(58) Field of Classification Search
CPC ........ G01N 15/06; G01N 33/00; G01N 33/48; G01N 21/00
USPC ........ 422/62, 63, 64, 65, 66, 67, 73, 81, 82, 422/82.01, 82.05, 501, 509, 510, 50, 68.1; 436/43, 518, 523, 533, 534, 535, 536, 47, 436/48, 49, 63, 66, 69, 823, 824
See application file for complete search history.

(56) References Cited

U.S. PATENT DOCUMENTS 5,730,941 A 3/1998 Lefevre et al.
6,043,205 A * 3/2000 Hoshiko et al. .............. 510/161
(Continued)

FOREIGN PATENT DOCUMENTS

| JP | 11108923 A | 4/1999 |
| JP | 11218538 A | 8/1999 |

(Continued)

OTHER PUBLICATIONS

ISA European Patent Office, Extended European Search Report of EP14168556, Oct. 1, 2014, 9 pages.

*Primary Examiner* — Brian J Sines
(74) *Attorney, Agent, or Firm* — Alleman Hall McCoy Russell & Tuttle LLP

(57) ABSTRACT

A blood analysis apparatus configured such that a nozzle sucks a predetermined amount of a blood specimen in a specimen container, and dispenses the specimen to each blood cell counting part which obtains count data, and a control part processes the count data to perform blood analysis. In this apparatus, two or more blood cell counting parts (basophil counting part, LMNE counting part, red blood cell counting part, white blood cell counting part) are constituted to obtain the count data of the same particular blood cell type (white blood cells), and the control part calculates the ratio or number of the existing blood cell from each count data, and judges whether the amount of the blood specimen sucked in the nozzle is normal or insufficient by comparing respective calculation results to determine whether they are within the predetermined allowable ranges.

3 Claims, 3 Drawing Sheets

(56) References Cited

U.S. PATENT DOCUMENTS

| | | | |
|---|---|---|---|
| 6,106,778 A * | 8/2000 | Oku et al. | 422/50 |
| 6,146,592 A * | 11/2000 | Kawashima et al. | 422/67 |
| 6,197,255 B1 * | 3/2001 | Miyake et al. | 422/64 |
| 6,333,197 B1 | 12/2001 | Le Comte et al. | |
| 6,440,369 B1 * | 8/2002 | Oonuma et al. | 422/64 |
| 6,605,213 B1 * | 8/2003 | Ammann et al. | 210/222 |
| 7,250,303 B2 * | 7/2007 | Jakubowicz et al. | 436/54 |
| 8,062,591 B2 * | 11/2011 | Yamamoto | 422/63 |
| 2010/0104169 A1 | 4/2010 | Yamada | |
| 2011/0194977 A1 | 8/2011 | Miyamura et al. | |

FOREIGN PATENT DOCUMENTS

| | | |
|---|---|---|
| JP | 2004-257768 A | 9/2004 |
| JP | 2005-062137 A | 3/2005 |
| JP | 2011-180117 A | 9/2011 |

\* cited by examiner

BLOOD ANALYSIS APPARATUS

FIELD OF THE INVENTION

The present invention relates to a blood analysis apparatus having a function to automatically perform counting and measurement such as classification, counting and the like of blood cells.

BACKGROUND OF THE INVENTION

Red blood cells, platelets and white blood cells, which are blood cells, change in number variously reflecting the condition of the living body. For example, red blood cells are mainly involved in the transportation of oxygen and change in number according to symptoms such as anemia, polycytemia and the like. In acute leukemia, moreover, red blood cells, platelets and neutrophils decrease and, among white blood cells, when blast cells, which are supposed to become granulocytes, become cancerous and blast cells are present in not less than 3%, acute myeloid leukemia develops, and when lymphocytes become cancerous and blast cells are present in less than 3%, acute lymphocytic leukemia develops.

Thus, the ratio of blood cells varies depending on the disease.

Therefore, blood analysis involving counting the blood cells according to the kind thereof, and determining the frequency distribution relating to the number, form, ratio and the like, is an important measurement for diagnosis in medical care and the like.

As methods for counting blood cells in a blood specimen (blood cell counting method), an impedance method utilizing changes in electrical characteristics, flow cytometry which is an optical technique, a light-focused flow impedance method which is a combination of the aforementioned impedance method and flow cytometry and the like are known, and blood cell counting apparatuses (blood analysis apparatuses) configured to perform these methods are also known.

Counting in the field of blood analysis means not only the simple counting of blood cells but also measuring which particles having what volume are present and in what number.

Moreover, a hemolysis treatment, a contraction treatment, a staining treatment and the like are applied as appropriate to a blood specimen to distinguish red blood cells from white blood cells, and further classifying white blood cells, neutrophils, eosinophils, basophils, monocytes and lymphocytes and counting them (what is called the classification of white blood cells into 5 types).

The mechanism of FIG. 1 is the mechanism of the main part of the blood analysis apparatus configured to count red blood cells and classify white blood cells into 5 types. As shown in FIG. 1, when a specimen container 1 containing a blood specimen is set at a predetermined position, a sampling nozzle 2 (a long and thin pipe which is also called a "needle") moves to suck the blood specimen in the specimen container 1, and discharges the same into each chamber (31, 32, 33, 34) in exclusive blood cell counting part 3, after which a counting device formed in or connected to the chamber obtains measurement data, and a control part (not shown) processes the measurement data and analyzes the frequency distribution and the like. Each blood cell counting part is composed of a chamber, which is a container receiving a blood specimen, and includes the device for performing the above-mentioned impedance method, flow cytometry and light-focused flow impedance method according to the blood cells to be counted, which operates according to the control part (e.g., computer). The obtained count data are sent to the control part. The details of each blood cell counting part are as mentioned below.

The sampling nozzle can move vertically and downwardly-upwardly due to the probe unit 6 provided with a moving mechanism 61 and a horizontally moving mechanism 62. The movements of inserting the sampling nozzle into the specimen container and each chamber to perform sucking and discharge are controlled by the control part (e.g., computer).

In a preferable embodiment, chambers formed to constitute each blood cell counting part include, as shown in FIGS. 1 and 3, BASO chamber 31 in the basophil counting part, a chamber 32 of the blood cell counting part for counting lymphocytes, monocytes, neutrophils and eosinophils, RBC chamber 33 in the red blood cell counting part, and WBC chamber 34 in the white blood cell counting part (for white blood cell counting, HGB analysis).

In the following explanation, the blood cell counting part for counting the aforementioned lymphocytes, monocytes, neutrophils and eosinophils is also referred to as a "LMNE counting part", taking each first letter from "lymphocyte", "monocyte", "neutrophil" and "eosinophil". Also, chamber 32 in FIG. 1, which is formed in the LMNE counting part, is also referred to as a "LMNE chamber". In the embodiment of FIG. 3, a flow cell (not shown) is connected to the LMNE chamber 32, and adapted to perform a necessary treatment with a reagent, performing the above-mentioned light-focused flow impedance method in the flow cell, and counting the aforementioned lymphocytes, monocytes, neutrophils and eosinophils.

In FIG. 1, the chamber shown by symbol 7 is a cleaning chamber for blood cell counting wherein the blood adhered to the sampling nozzle (hereinafter to be also referred to as "nozzle") is washed or cleaned, or an excess blood specimen in the nozzle is discarded.

In the blood analysis apparatus shown in FIG. 1, the nozzle 2, as shown in FIG. 2, sucks a predetermined amount of a blood specimen 100 into its long and thin conduit at one time, and discharges the same into each chamber in the blood cell counting part 3. To be more specific, the blood specimen in the first section A1 of the nozzle is discharged into a WBC chamber 34, the blood specimen in the second section A2 is discharged into a BASO chamber 31, and the blood specimen in the third section A3 is discharged into an LMNE chamber 32.

In each blood cell counting part containing the dispensed blood specimen, the count data specific to each blood cell counting part is obtained under the control of the control part, the count data obtained from each blood cell counting part are processed in the control part (not shown), and each of the object blood cells is analyzed for the frequency distribution and the like.

To precisely perform sucking, dispensing and discharging a predetermined amount of a blood specimen, the nozzle 2 is connected to a quantitative pump (not shown), and a working fluid 110 such as a diluting liquid and the like is filled in a conduit line between the nozzle 2 and the quantitative pump, whereby a sucking force F1 by the quantitative pump and a discharging force F2 can be accurately transmitted to the nozzle (FIG. 2). A predetermined amount of air 120 is interposed between the working fluid 110 and the blood specimen 100, whereby the working fluid 110 is separated from the blood specimen 100 (FIG. 2).

A method and mechanism thereof for dividing the predetermined amount of the blood specimen 100 sucked in the nozzle at predetermined ratios in the longitudinal direction of the conduit and sequentially dispensing the same in the chambers in each blood cell counting part are explained in detail in, for example, JP-A-11-218538.

As mentioned above, a problem associated with sucking a predetermined amount of a blood specimen in a sampling nozzle and dispensing the same in each blood cell counting part is a phenomenon of insufficient sucking of a blood specimen in the nozzle (insufficient specimen-sucking amount, also called sample short). This phenomenon includes not only a simple failure of a blood specimen to reach a predetermined height of the sampling nozzle, but also mixing of air bubble(s) in the middle part of the nozzle to cause insufficient specimen-sucking amount even when the blood specimen has reached a predetermined height of the sampling nozzle.

The insufficient specimen-sucking amount is developed when the amount of a blood specimen in a specimen container is not sufficient and, as the factors on the side of the apparatus, fouling and clogging of the nozzle and piping, operation failure of the driving part and the like.

When an insufficient specimen-sucking amount occurs, the results of blood cell counting in a blood cell counting part, in which a blood specimen is not sufficiently distributed, are different from those that should have been obtained, and may lead to incorrect diagnosis. For example, in the embodiments of FIGS. 1 and 2, when an insufficient specimen-sucking amount wherein the specimen only reaches half way up to a third section A3 of the nozzle is developed, the following occurs. That is, in the LMNE counting part wherein the blood specimen in this section is dispensed, treatments such as mixing with a predetermined quantity of a reagent, hemolysis of red blood cells, staining and fixing of the object blood cell, and transfer thereof to a flow cell are performed in an LMNE chamber and the blood cells are counted. Therefore, the results of counting become lower than those when the specimen suck amount is normal.

Conventionally, insufficiency of specimen has been pointed out as a problem of various analysis apparatuses. Solution to the problem has been sought by taking note of the specimen in a specimen container, and imaging the amount thereof for detection or confirming the sucked amount of the specimen by using a sensor. However, these measures require a new sensor and an increased number of control circuits in the analysis apparatus, thus rendering the apparatus configuration more complicated.

When a blood specimen is sucked with a sampling nozzle, as shown in FIGS. 1 and 2, since stainless steel with high corrosion resistance is used as a material of the nozzle, it is difficult to directly detect the amount of the blood specimen sucked in the sampling nozzle by a sensor.

The problem of the present invention is to provide a blood analysis apparatus provided with a function to determine whether the amount of a blood specimen sucked in a sampling nozzle has reached a predetermined amount or is insufficient by a new technique.

SUMMARY OF THE INVENTION

The present invention has the following constitutions.
(1) A blood analysis apparatus comprising at least:
    a plurality of blood cell counting parts;
    a sampling nozzle; and
    a control part which controls operations of the blood cell counting parts and the sampling nozzle, and performs data processing of blood analysis;
    wherein
    the sampling nozzle is adapted to be controlled by the control part:
        to suck a predetermined amount of a blood specimen, which is contained in a specimen container to be set in the blood analysis apparatus; and then
        to dispense the predetermined amount of blood specimen to each of the blood cell counting parts at a predetermined ratio,
    each blood cell counting part is adapted to be controlled by the control part, to obtain the count data for each blood cell counting part,
    the control part is adapted to process the count data from each blood cell counting part and to perform blood analysis, and wherein
    two or more blood cell counting parts are each adapted to obtain the count data about a same particular kind of blood cells, in addition to the count data that each blood cell counting part originally intends to obtain, and
    the control part is adapted:
        to respectively calculate a ratio or number of the existing particular kind of blood cells from the count data about the particular kind of blood cells;
        to compare the calculation results to determine whether the calculation results are within a predetermined allowable range, thereby
        to determine whether the amount of the blood specimen sucked in the sampling nozzle was normal or insufficient.
(2) The blood analysis apparatus of (1),
    wherein, in the sampling nozzle, a predetermined section in a full-length of the predetermined amount of the blood specimen to be sucked is further divided into sections at predetermined ratios,
    wherein, the above-mentioned particular kind of blood cells is white blood cells,
    wherein, the divided sections include a section for white blood cell counting, which is determined to be dispensed to a blood cell counting part that performs white blood cell counting, and
    wherein, the apparatus is adapted such that a blood specimen in the section for white blood cell counting is essentially used for comparison of the ratio or number of the existing white blood cells.
(3) The blood analysis apparatus of (1) or (2),
    wherein the above-mentioned particular kind of blood cells is white blood cells,
    wherein two or more blood cell counting parts are selected from:
        a white blood cell counting part;
        a basophil counting part; and
        a blood cell counting part for counting lymphocytes, monocytes, neutrophils and eosinophils in white blood cells;
    and wherein the two or more blood cell counting parts essentially include the white blood cell counting part.

DETAILED DESCRIPTION OF THE INVENTION

The present invention takes note of the fact that the count data about the same particular (predetermined) blood cells are obtained in each exclusive blood cell counting part, wherein the blood specimen was dispensed. Using the respective count data, the ratio or number of the existing particular blood cells is calculated, and the calculation results are collated to detect whether the amount of the blood specimen sucked in the nozzle is normal or insufficient.

Figure 1:
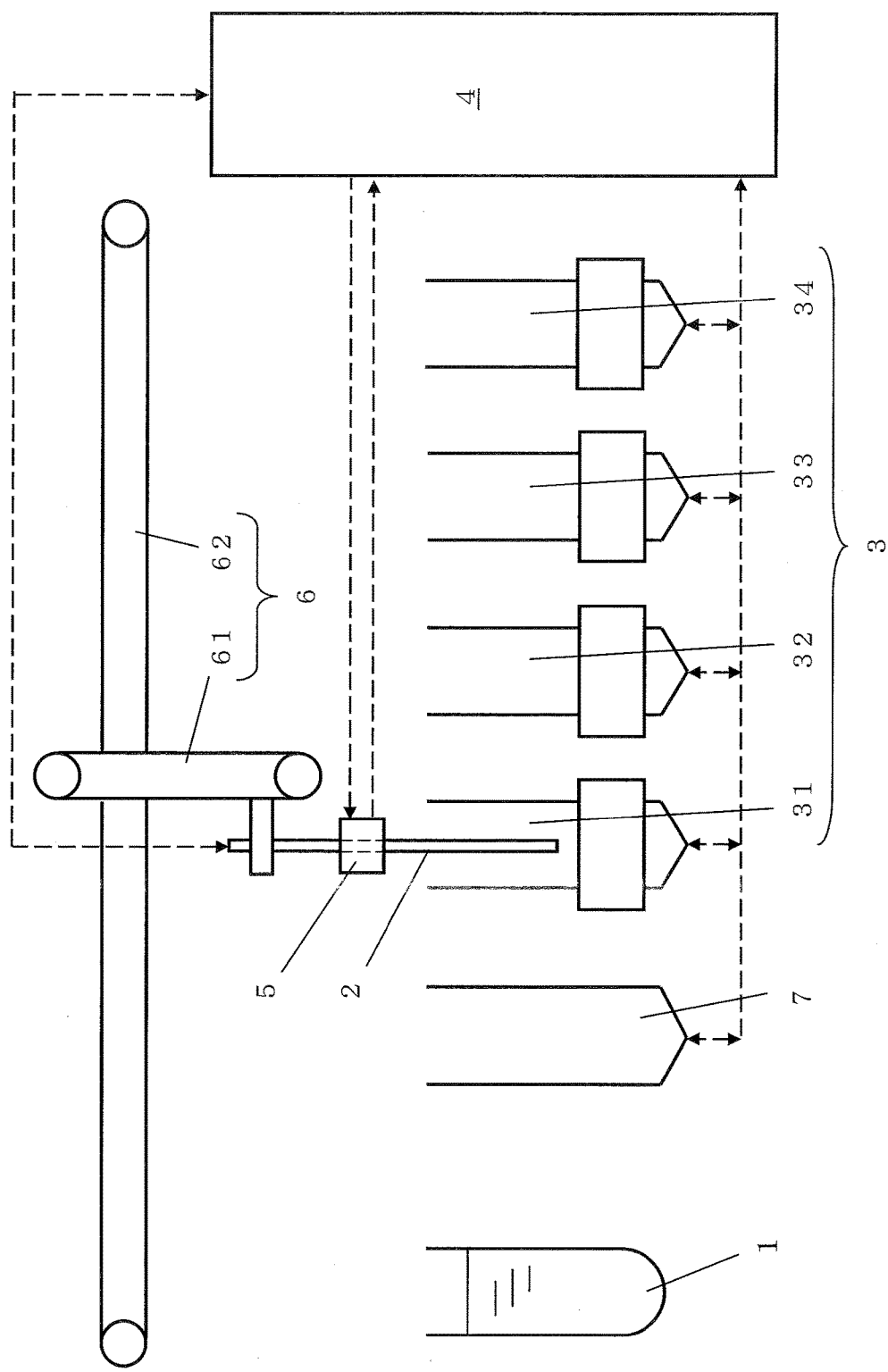
FIG. 1 schematically shows one example of the configuration of the main part of a conventional blood analysis apparatus and that of the present invention. While each chamber in the blood cell counting part has a corner bottom, actually, it preferably has appropriate roundness in consideration of the smooth outflow and inflow of the liquid.

For example, a blood analysis apparatus for classification of white blood cells into 5 types is provided with a basophil counting part configured to have a BASO chamber 31; an LMNE counting part configured to have an LMNE chamber 32 and a flow cell (not shown); and a white blood cell counting part configured to have a WBC chamber 34 (which also performs HGB analysis), as shown in FIG. 1.

While basophils are counted in the basophil counting part, the count data include the data relating to the white blood cells as a whole (detail is mentioned later). Similarly, counting to form an LMNE matrix is also performed in the LMNE counting part, the count data include the data relating to the white blood cells as a whole (detail is mentioned later). Also, the count data obtained in a white blood cell counting part are used to accurately count the number of white blood cells.

The amount of the blood specimen to be dispensed to a chamber in each blood cell counting part is predetermined, and the dilution ratio of each chamber, flow velocity during counting, count time and the like are also predetermined.

Therefore, when the number of white blood cells per unit volume of the sample liquid diluted to a particular value (i.e., ratio or number of the existing white blood cells) is calculated from the count data obtained in each chamber, the calculation results of the diluted sample liquid vary according to the amount of the original, dispensed blood specimen. Accordingly, when the amount of the blood specimen actually dispensed to each chamber is the predetermined correct amount, the calculation results of the ratio or number of the existing white blood cells in the sample liquid diluted to a particular diluting value, which are obtained from the count data of each chamber, must be identical or close to each other, within a predetermined allowable range.

Taking note of the particular blood cell type such as white blood cells, comparing and collating the count results of the blood cell from each chamber and examining whether the cell is within a predetermined allowable range, whether the amount of the blood specimen sucked in the nozzle was normal or insufficient can be determined from the comparison results.

According to the determination method of the present invention, addition of hardware such as a mechanism, a sensor and the like, aiming at detection of insufficient specimen-sucking amount, is not necessary, and the safety of the blood analysis apparatus can be increased without raising the cost.

The configuration of the blood analysis apparatus of the present invention is explained in more detail in the following by referring to Examples.

FIG. 1 is a partially-enlarged view showing the characteristic configurational part in the embodiment of the blood analysis apparatus of the present invention. While the present invention requires at least two blood cell counting parts for the comparison judgment, in the embodiment of this Figure, a BASO chamber 31 in the basophil counting part and an LMNE chamber 32 in the LMNE counting part are provided, so that the classification of white blood cells into 5 types can be performed, in addition to the RBC chamber 33 in the red blood cell counting part and the WBC chamber 34 that also performs HGB analysis in the white blood cell counting part. While the LMNE counting part accompanies a flow cell, it is not shown in the Figure.

Figure 3:
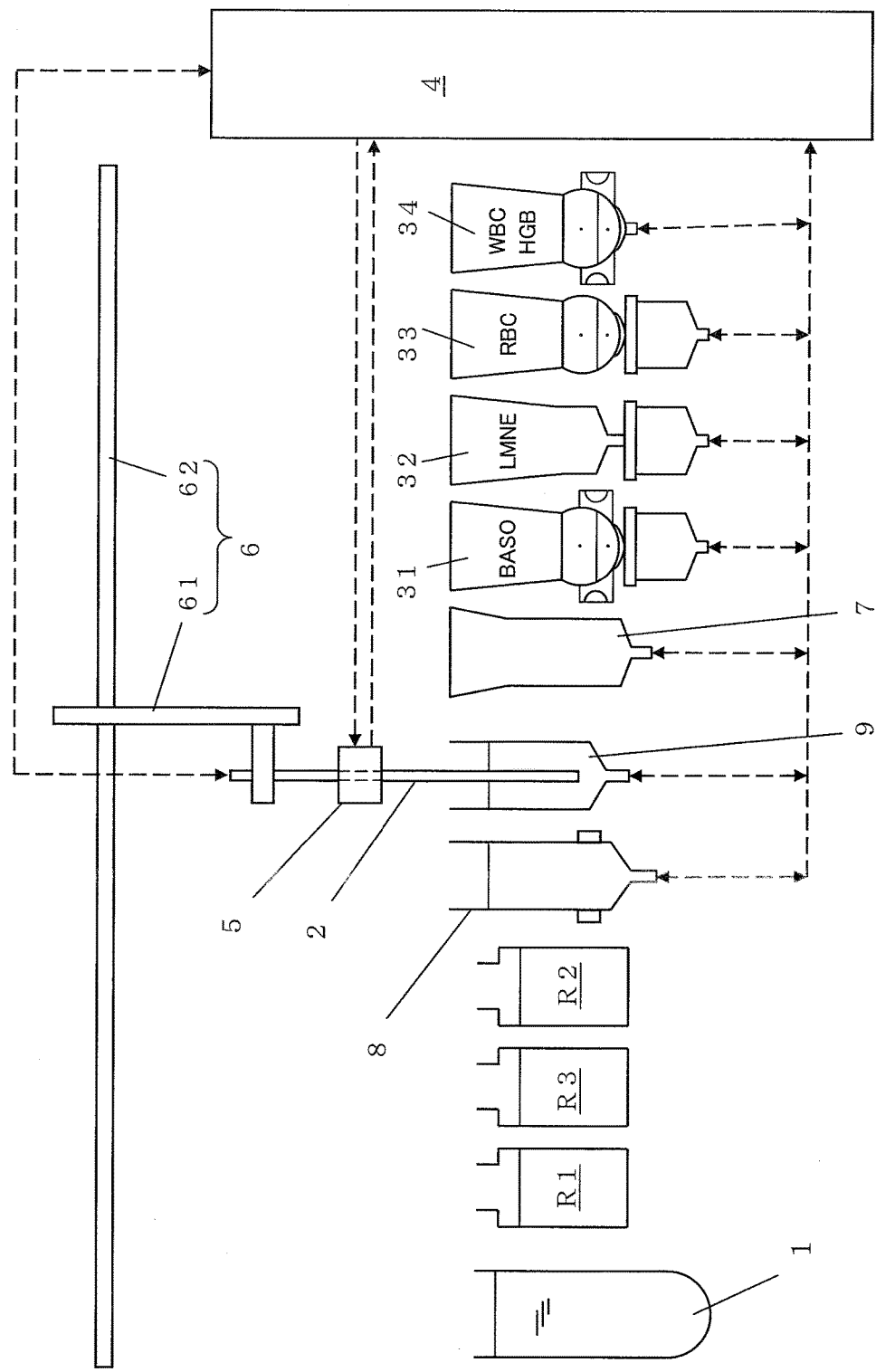
FIG. 3 schematically shows the configuration of the main part of a more preferable embodiment of a conventional blood analysis apparatus and that of the present invention.

A sampling nozzle cleaning device 5 accompanies the sample nozzle, which is configured to clean the outer surface of a nozzle with a diluting liquid to the sampling nozzle 2. The nozzle cleaning device 5 has an annular-shaped main part, and the nozzle passes through the central through-hole thereof (the tip of the nozzle 2 is located below the nozzle cleaning device). The diluting liquid is a liquid usable for diluting a blood specimen for the below-mentioned counting, such as saline, phosphate buffer diluting liquid and the like, and is also used for washing. Therefore, when nozzle 2 moves downwardly and upwardly, the annular-shaped main part of the nozzle cleaning device 5 relatively moves on the outer surface of the nozzle. The nozzle cleaning device 5 moves in the horizontal direction along with nozzle 2, and fixed at a certain height in the vertical direction. In a preferable embodiment, when the nozzle moves to the lowest part, a diluting liquid is discharged from the annular-shaped main part of the nozzle cleaning device, whereby the whole outer peripheral surface of the nozzle is washed. In FIGS. 1 and 3, a piping to supply a diluting liquid to nozzle cleaning device 5 is shown with a broken line.

In the embodiment of FIG. 1, a specimen container 1 containing a specimen is set at a predetermined position in the apparatus, and the specimen container 1, a cleaning chamber 7 for blood cell counting chambers 31-34 of each blood cell counting part are aligned along a straight line extending in the horizontal direction. Due to a probe unit 6, the nozzle 2 moves in the horizontal direction along the aforementioned straight line and moves in the vertical direction to repeatedly enter into or go out from specimen containers and each chamber for sucking a blood specimen from the specimen container and dispensing the same to each chamber. An exhaust pipe shown with a broken line is connected to the lower end part of the cleaning chamber for blood cell counting and each blood cell counting chamber, whereby a waste liquid is delivered to a waste liquid container (not shown), through an electromagnetic valve device 4, by a pump (not shown). A cleaning chamber 7 for blood cell counting is an exclusive chamber for cleaning the nozzle after dispensing the blood specimen.

Control of operation of the probe unit, control of sucking and discharging of the nozzle, and control of an electromagnetic valve device are all executed by the control part. The control part is configured to count and measure blood cells in communication with each blood cell counting chamber, and analyze the obtained count data and measurement data.

As the control part, a computer is appropriate, and various external operation units and a drive unit for each actuator may be connected as appropriate. The kind and arrangement of each chamber, and the operation mechanism itself of the nozzle may be similar to those of the conventionally known apparatuses.

The important characteristic of the present invention is, as mentioned above, that the control part utilizes the count data of the same particular blood cell type (white blood cell in this embodiment) obtained for each exclusive chamber, to calculate the ratio or number of the existing white blood cells from the count data, and compare the ratio or number to determine whether the calculation results are within the predetermined allowable range, based on which whether the amount of the specimen sucked in a nozzle 2 is normal or insufficient is judged. The judgment operation is explained in detail by reference to specific examples.

Figure 2:
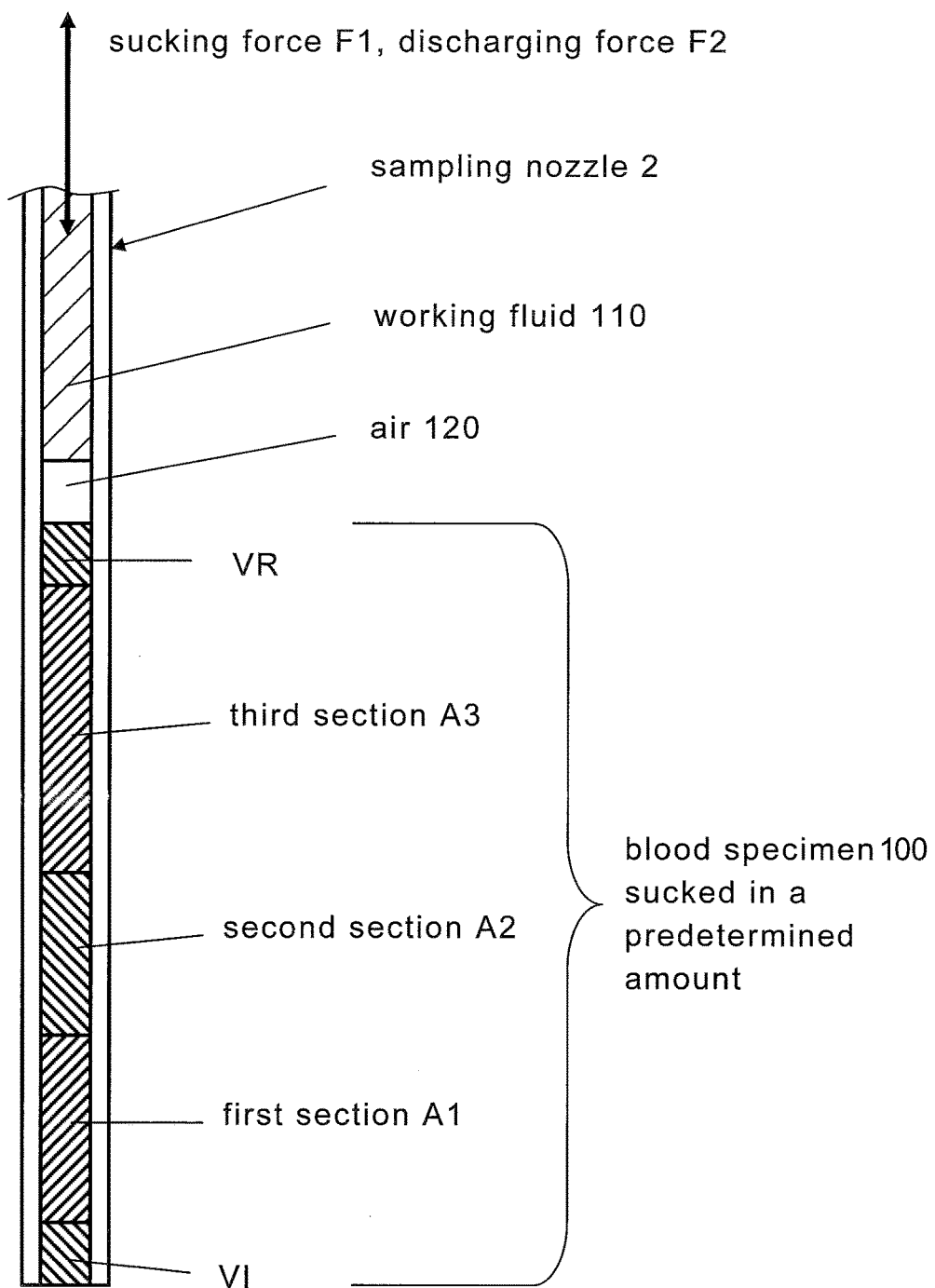
FIG. 2 explains how a blood specimen sucked in a sampling nozzle is divided and dispensed conventionally and in the present invention.

In FIG. 1, the nozzle 1 first sucks a predetermined amount of a blood specimen from the specimen container. The state of sucking of predetermined amounts of a blood specimen in the nozzle is shown in FIG. 2.

The conventionally-known techniques may be referred to for the mechanism of the probe unit 6, which horizontally moves the nozzle along a predetermined pathway, as well as downwardly and upwardly. Examples thereof include a rectilinear mechanism using a timing-belt (or V-belt) which has a shape of an endless belt (looped belt) and the like, a rectilinear mechanism by a ball screw, a rectilinear mechanism by a cylinder, a rectilinear mechanism by other actuator, a moving mechanism by a movable arm, which is a combination of these, and the like. In the embodiment shown in FIG. 1, the nozzle can move in the horizontal direction and the vertical direction by the timing belt 62, which is a moving mechanism in the horizontal direction, and a probe unit 6 having a timing belt 61 which is a moving mechanism in the upward and downward directions.

The nozzle reciprocates almost right above the specimen container and each chamber aligned and placed on a straight line, and descends or ascends at predetermined positions to perform sucking and discharge of specimen, and cleaning. Such movements are controlled by a computer and performed as programmed.

The sucked amount of the blood specimen and the ratio of dispensation thereof are not particularly limited, and sucked amounts by conventionally-known blood analysis apparatuses may be referred to.

In FIG. 2, in the full-length of a predetermined amount of a blood specimen 100 sucked in the nozzle 2, the blood specimen of section VI in the tip of the nozzle 2 is discarded in a cleaning chamber 7 for blood cell counting in an attempt to suppress dispersion in the volume of the blood specimen due to the surface tension of the tip end face, to eliminate contamination and the like.

Thereafter, the nozzle moves and discharges the blood specimen of the first section A1 of the nozzle into the WBC chamber 34.

Furthermore, the nozzle moves and discharges the blood specimen of the second section A2 into the BASO chamber 31.

Furthermore, the nozzle moves and discharges the blood specimen of the third section A3 into the LMNE chamber 32.

The blood specimen of the section VR remaining lastly may be used by the apparatus for other analyses or discarded as an excess portion in a cleaning chamber 7 for blood cell counting.

The blood specimen discharged in the WBC chamber 34 is diluted to a given concentration in the chamber, and partly distributed to RBC chamber 33.

[Processing in the White Blood Cell Counting Part]

The WBC chamber provided as a white blood cell counting part contains an electrode pair for measuring the white blood cell count by the impedance method, moreover, a light-irradiation part and a light-receiving part for measuring the absorbance by colorimetry (non-cyanogen method) and the like, and the hemoglobin concentration is measured. In the Figure, the mechanism of injecting the hemolysis agent, and a detailed mechanism for performing the impedance method are omitted. The same applies to other blood cell counting parts.

In a preferable configuration example, the blood specimen dispensed in the WBC chamber is diluted with a diluting liquid discharged in the chamber through a piping connected to a reagent port located at the upper part of the chamber. The WBC chamber is further added with a reagent for red blood cell hemolysis, wherein the final dilution rate of the blood specimen in the WBC chamber is, for example, about 1/250. Thereafter, the white blood cells are counted based on the impedance method in the WBC chamber.

A part of the specimen diluted first in the WBC chamber 34 is also distributed in the RBC chamber 33 to count the red blood cells therein. The RBC chamber 33 is a chamber for counting red blood cells and platelets, and provided with a device having an aperture and electrodes on the lower part of the chamber, so that the impedance method can be performed.

[Processing in the Basophil Counting Part]

The BASO chamber provided as a basophil counting part is an exclusive chamber configured to count basophils by the impedance method. The blood specimen dispensed to the BASO chamber is first diluted with a hemolysis agent for the basophil measurement, the agent is discharged into the chamber through a piping connected to a reagent port at an upper part of the chamber.

The dilution rate of the blood specimen in the BASO chamber is, for example, about 1/300.

In this embodiment, red blood cells are hemolysed in the BASO chamber, white blood cell components other than the basophils are constricted, and the white blood cells are counted based on the impedance method. Basophils and other white blood cells are distinguished based on the magnitude of the obtained pulse voltage (difference in the volume). Thus, the basophil counting part is an exclusive device for counting basophils; however, it also outputs the count results of the white blood cells as a whole.

Conventionally, the count results of the white blood cells as a whole, which are obtained in the basophil counting part, have not been particularly noted. In this embodiment, the count results of the white blood cells as a whole, which have not been utilized even though counted, are noted and utilized for comparison.

[Processing in the LMNE Counting Part]

First, lymphocytes (L), monocytes (M), neutrophils (N) and eosinophils (E) are reacted with a staining reagent in the LMNE chamber to count them in a flow cell.

The blood specimen dispensed to the LMNE chamber is first diluted with a staining reagent discharged into the chamber through a piping connected to a reagent port at an upper part of the chamber. A diluting liquid is further added to the LMNE chamber. The dilution rate of the blood specimen in the LMNE chamber is, for example, about 1/80.

The stained and diluted blood specimen is transferred to a flow cell, wherein lymphocytes, monocytes, neutrophils and eosinophils are counted based on the light-focused flow impedance method, and the data are processed in the control part to count the frequency per volume, which is shown in a scattergram such as an LMNE matrix and the like.

The count results according to the light-focused flow impedance method performed in the flow cell also include the measurement results by the impedance method in addition to the optical count results, and therefore, the obtained count data also include the count data of the basophils. That is, the LMNE counting part also outputs the count data of the white blood cells as a whole.

Like the BASO chamber, this embodiment takes note of the count data of the white blood cells as a whole, which have not been utilized even though counted, and utilizes the data for comparison.

In the present invention, at least two blood cell counting parts are each constituted to obtain count data of the same particular, predetermined blood cells, and compare and collate the data in the control part.

In this embodiment, note was taken of the fact that the count data of the white blood cells as a whole are the output of all the blood cell counting parts: the white blood cell counting part, basophil counting part, and LMNE counting part, and the aforementioned particular blood cell type is white blood cells, and the count data of white blood cells obtained in each counting part are compared and collated, and whether the amount of the blood specimen sucked in the first nozzle was normal or insufficient is determined.

In this embodiment, respective count data of the white blood cells obtained from the white blood cell counting part, basophil counting part, and LMNE counting part are processed in the control part, and the number of the existing white blood cells per unit volume of the diluted blood specimen is calculated and compared with each other. The numerical values to be compared may be a ratio which is a ratio relative to the standard number per unit volume or a parameter equivalent thereto.

As explained above, the amount of the blood specimen to be dispensed to each blood cell counting part is a predetermined value, and the dilution rate in each chamber, flow velocity during counting, count time and the like are all predetermined values. Therefore, the numbers of the existing white blood cells per unit volume of diluted blood specimen can be calculated from the measurement data and compared with each other.

The control part judges that the aforementioned amount of the blood specimen sucked in a sampling nozzle is normal when the comparison results match within the predetermined allowable range. It conversely points out the possibility of insufficient sucked amount with a warning to the user, when the results are outside the allowable range.

The aforementioned allowable range can be appropriately determined in consideration of error in the dispensed amount in each blood cell counting part, dilution error, count error and the like and based on the statistics obtained by previous experiments using, for example, standard or typical specimen, such as [within ±20% being normal] and the like.

In this embodiment, white blood cells were used as a particular blood cell type for the detection of insufficient specimen-sucking amount, and the count data of white blood cells obtained in a plurality of blood cell counting parts are utilized. As long as the count data of the same blood cell type are obtained in two or more blood cell counting parts, the blood cell type may be red blood cells or other type of blood cells. For example, in the case of red blood cells, Hgb concentration may be compared.

As shown in FIG. 2, a given section in the full length of the predetermined amount of a blood specimen sucked in the nozzle 2 is divided into sections at a predetermined ratio to be dispensed to the corresponding blood cell counting parts. In the embodiment of FIG. 2, the sections are first section-third section.

In the present invention, it is recommended that the count data of the blood cell counting parts, to which the blood specimen in the predetermined sections determined to be dispensed to the blood cell counting part relating to the white blood cell counting (sections for white blood cell counting) has been dispensed, are compared for the detection of insufficient specimen-sucking amount. This is because white blood cells are further classified into 5 types or more, therefore a plurality of blood cell counting parts capable of outputting the count data of white blood cell are, in many cases, included in the blood cell counting parts, as in the apparatus of FIG. 1.

The combination of the sections to be compared in the embodiment of FIG. 1 may be
[combination of a section for the LMNE counting part (third section) and a section for the basophil counting part (second section)];
[combination of a section for the LMNE counting part (third section) and a section for the white blood cell counting part (first section)];
[combination of a section for the basophil counting part (second section) and a section for the white blood cell counting part (first section)], and the like.

In a more preferable embodiment of the aforementioned embodiment, the count data of the white blood cells obtained from respective blood cell counting parts, to which the blood specimen in the first section-third section has been dispensed, are compared. In this manner, the detection of insufficient specimen-sucking amount becomes more accurate.

Moreover, as in the embodiment of FIG. 1, when the count data of white blood cells are utilized for the detection of insufficient specimen-sucking amount and a white blood cell counting part is included in a plurality of blood cell counting parts, the count data of the white blood cell counting part are to be essentially utilized, since the most accurate count data of the white blood cell counting part can be obtained by utilizing the count data of white blood cells.

In the embodiment of FIG. 1, the blood cell counting part includes a white blood cell counting part, a basophil counting part, and an LMNE counting part. Two or more blood cell counting parts essentially including the white blood cell counting part are selected from them.

In the embodiments of FIGS. 1 and 2, the blood specimen in the first section of the nozzle is dispensed to the white blood cell counting part, the blood specimen in the second section is dispensed to the basophil counting part, and the blood specimen in the third section is dispensed to the LMNE counting part. In which section and to which chamber in the blood cell counting part a blood specimen is to be dispensed may be changed as appropriate for the detection of the insufficient specimen-sucking amount.

A mechanism capable of performing a preferable method such as an impedance method, flow cytometry, a light-focused flow impedance method and the like may be formed in each blood cell counting part according to the count target blood cell to provide a constitution enabling counting in each control part.

The impedance method is also called an electric resistance method, and is a technique wherein an aperture and an electrode pair are formed in the flow channel for a sample liquid, the electrodes are provided to interpose the aperture between them, and the volume of the blood cell passing through the aperture is measured based on the changes in the electrical characteristics (particularly changes in the pulse voltage) between the electrodes (e.g., JP-A-2004-257768, JP-A-2011-180117, JP-A-2005-62137).

In the apparatus of JP-A-2011-180117, the flow channel on the downstream side of the aperture diverges in a unique configuration and, in the apparatus of JP-A-2005-062137, a pair of electrodes is set on the downstream side of the aperture in a unique configuration. The basic principle of the electrical resistance method, wherein an aperture is positioned between a pair of electrodes and the size of the particles is determined, is the same as that mentioned above.

Flow cytometry is a technique wherein a predetermined irradiation light is irradiated as a beam light focused on the blood cells in a sample liquid advancing through a flow channel, and the blood cells are distinguished from optical characteristics such as light scattering, light absorbance and the like resulting therefrom (e.g., JP-A-8-327529).

The light-focused flow impedance method enables both optical counting by flow cytometry and counting through electrical characteristics by the impedance method by incorporating an aperture and an electrode pair for the impedance method in the flow channel of a flow cell (flow cytometer).

In the apparatus of FIG. 3, an immunity measurement function has been further added to the apparatus of FIG. 1.

In the apparatus of FIG. 3, a constitution capable of measuring the content of C-reactive protein in blood (hereinafter to be referred to as CRP) is added, wherein CRP measuring chamber 8 as a CRP measuring part, cleaning chamber 9 for immunity measurement, reagent containers containing reagents (R1, R2, R3) for CRP measurement, a cleaning chamber 7 for blood cell counting, and chamber 3 of each blood cell counting part (BASO chamber 31 of basophil counting part, LMNE chamber 32 of the LMNE counting part, RBC chamber 33 of the red blood cell counting part, WBC chamber 34 of the white blood cell counting part) are set at predetermined positions.

The cleaning chamber 9 for immunity measurement is also an exclusive chamber for the final cleaning of the nozzle, and intends to shorten the operation time of the whole apparatus by simultaneously performing the final cleaning of the nozzle in the cleaning chamber 9, while the CRP measurement is being performed in the CRP measuring chamber 8.

The immunity measurement function may be not only CRP measurement but also an immunological measurement such as analysis of components in blood plasma and the like. CRP value is frequently measured as a representative inflammatory marker in clinical laboratory tests (bacterial infections, etc.), and is an important measurement item for blood analysis apparatuses.

In the embodiment shown in FIG. 3, a CRP measuring chamber is a chamber configured to be able to optically measure the CRP value according to the latex coagulating method, which is provided with a light-irradiation part and a light detection part for the CRP measurement at the lower wall surfaces of the chamber, and configured to be able to appropriately stir the liquid contained inside. An exhaust pipe shown with a broken line is connected to a lower end part of the CRP measuring chamber 8, whereby the waste liquid is transferred to a waste liquid container via an electromagnetic valve device 4 and a pump P. In addition, the reagent containers contain hemolysis reagent (R1), buffer liquid (R2), and anti-human CRP sensitized latex immunoreagent (R3).

In the case of FIG. 3, like FIG. 1, the ratio or number of the existing white blood cells is calculated from the count data of white blood cells respectively obtained from a white blood cell counting part, a basophil counting part, and an LMNE counting part, and compared and collated to determine whether the amount of the blood specimen sucked in the nozzle is normal or insufficient.

INDUSTRIAL APPLICABILITY

According to the present invention, whether the amount of the blood specimen sucked in the nozzle reached the predetermined amount or is insufficient can be confirmed based on the count data and without adding a detecting mechanism and hardware such as a sensor and the like. This has increased the reliability of a blood analysis apparatus without increasing the production cost of the apparatus or production cost of the hardware side.

This application is based on a patent application No. 2013-105519 filed in Japan, the contents of which are incorporated in full herein.

The invention claimed is:

1. A blood analysis apparatus comprising at least:
   a plurality of blood cell counting parts;
   a sampling nozzle;
   a specimen container containing a blood specimen to be set in the blood analysis apparatus; and
   a controller programmed to control operations of the blood cell counting parts and the sampling nozzle, and perform data processing of blood analysis;
   wherein the controller is further programmed to:
      control the sampling nozzle to suck a predetermined amount of the blood specimen and then dispense the predetermined amount of the blood specimen to each of the blood cell counting parts at a predetermined ratio,
      control each of the blood cell counting parts to obtain count data for each blood cell counting part, and
      control two or more blood cell counting parts to obtain the count data about a particular, same kind of blood cell, in addition to the count data that each blood cell counting part originally intends to obtain, and
   wherein the controller is further programmed to:
      process the count data from each of the blood cell counting parts and perform blood analysis;
      respectively calculate a ratio or number of the existing particular kind of blood cells from the count data about the particular kind of blood cell;
      compare the calculation results to determine whether the calculation results are within a predetermined allowable range, thereby
      determine whether the amount of the blood specimen sucked in the sampling nozzle was normal or insufficient.

2. The blood analysis apparatus according to claim 1,
   wherein said particular kind of blood cells is white blood cells,
   wherein the two or more blood cell counting parts are selected from:
      a white blood cell counting part;
      a basophil counting part; and
      a blood cell counting part for counting lymphocytes, monocytes, neutrophils and eosinophils in the white blood cells;
   and wherein the two or more blood cell counting parts essentially include the white blood cell counting part.

3. The blood analysis apparatus according to claim 1,
   wherein the controller is further programmed to control the sampling nozzle such that a predetermined section in a full-length of the predetermined amount of the blood specimen to be sucked is further divided into sections at predetermined ratios,
   wherein, said particular kind of blood cells is white blood cells,
   wherein, the divided sections include a section for white blood cell counting, which is determined to be dispensed to a blood cell counting part that performs white blood cell counting, and wherein the controller is further programmed to use a blood specimen in the section for white blood cell counting for comparison of the ratio or number of the existing white blood cells.

* * * * *